(12) United States Patent
Rocci et al.

(10) Patent No.: US 10,869,704 B2
(45) Date of Patent: Dec. 22, 2020

(54) METACARPAL NECK PLATE

(71) Applicant: DePuy Synthes Products, LLC, Raynham, MA (US)

(72) Inventors: Mirko Rocci, Zuchwil (CH); Fabienne Fischer, Zuchwil (CH); Franco Cicoira, Selzach (CH); Martin Langer, Munster (DE)

(73) Assignee: DePuy Synthes Products, Inc., Raynham, MA (US)

( * ) Notice: Subject to any disclaimer, the term of this patent is extended or adjusted under 35 U.S.C. 154(b) by 1723 days.

(21) Appl. No.: 14/320,470

(22) Filed: Jun. 30, 2014

(65) Prior Publication Data

US 2015/0374421 A1 Dec. 31, 2015

(51) Int. Cl.
*A61B 17/88* (2006.01)
*A61B 17/80* (2006.01)

(52) U.S. Cl.
CPC .................. *A61B 17/8061* (2013.01)

(58) Field of Classification Search
None
See application file for complete search history.

(56) References Cited

U.S. PATENT DOCUMENTS

| | | | |
|---|---|---|---|
| 5,897,555 A | 4/1999 | Clyburn et al. | |
| 6,096,040 A | 8/2000 | Esser | |
| 6,565,571 B1 | 5/2003 | Jackowski et al. | |
| 7,179,260 B2 | 2/2007 | Gerlach et al. | |
| 7,537,604 B2 | 5/2009 | Huebner | |
| 7,695,502 B2 | 4/2010 | Orbay et al. | |
| 7,867,260 B2 | 1/2011 | Meyer et al. | |
| 8,366,751 B2 | 2/2013 | Pfefferle et al. | |
| 2001/0011172 A1 | 8/2001 | Orbay et al. | |
| 2007/0239163 A1 | 10/2007 | Strnad et al. | |
| 2009/0198285 A1 | 8/2009 | Raven, III | |
| 2009/0281543 A1 | 11/2009 | Orbay et al. | |
| 2013/0211459 A1* | 8/2013 | Horan ................ A61B 17/8052 606/280 |

FOREIGN PATENT DOCUMENTS

| | | |
|---|---|---|
| CN | 2124683 | 12/1992 |
| CN | 201759658 U | 3/2011 |
| CN | 202568423 | 12/2012 |

(Continued)

*Primary Examiner* — Sameh R Boles
(74) *Attorney, Agent, or Firm* — Fay Kaplun & Marcin, LLP

(57) ABSTRACT

A bone plate sized and shaped for fixation to a metacarpal includes a head extending from a first end to a second end and having first and second fixation element holes extending therethrough along first and second fixation element hole axes, wherein the first hole axis diverges from the second hole axis on a bone facing side of the plate, the head having a first notch on the first end centered on the central longitudinal axis, the first notch formed as a indentation on an outer wall of the bone plate sized and shaped to accommodate a collateral ligament when the plate is fixed to a metacarpal in a desired position and a shaft extending from the second end of the head to a third end along the central longitudinal axis, the shaft including an elongated fixation element hole elongated in a direction parallel to the central longitudinal axis.

13 Claims, 1 Drawing Sheet

(56) References Cited

FOREIGN PATENT DOCUMENTS

| EP | 1707227 | 10/2006 |
|---|---|---|
| EP | 2623059 | 8/2013 |
| FR | 2924593 | 6/2009 |
| TW | 201206390 | 2/2012 |
| TW | 201320953 | 6/2013 |

* cited by examiner

METACARPAL NECK PLATE

FIELD OF THE INVENTION

The exemplary embodiments generally relate to plates for the fixation of fractures of bones in the hand and methods of implanting these plates on bone.

BACKGROUND

Current systems and methods for the fixation of certain fractures are limited in the placement and orientation of bone fixation plates over the bone. For example, plates for the fixation of fractures of the fifth metacarpal are confined to a limited placement of the plate dictated heavily by the construction of the plate and not by the location/type of the fracture or an optimized position that might be selected by a surgeon absent these limitations imposed by the plate construction. More specifically, plates for fixation of fractures of the fifth metacarpal, also known as boxer's fractures, are generally limited to a placement over only predetermined portion of a lateral surface of the bone with a first portion of the plate being dorsal and a second portion of the plate being lateral. Depending on the type of fracture, this placement may not be optimal and limiting placement to this arrangement does not provide the surgeon with the freedom to select an optimal placement for many fracture types.

SUMMARY

The exemplary embodiments are directed to a bone plate sized and shaped for fixation to a metacarpal comprising a head extending from a first end to a second end and having first and second fixation element holes extending therethrough along first and second fixation element hole axes, wherein the first hole axis diverges from the second hole axis on a bone facing side of the plate, the head having a first notch on the first end centered on the central longitudinal axis, the first notch formed as a indentation on an outer wall of the bone plate sized and shaped to accommodate a collateral ligament when the plate is fixed to a metacarpal in a desired position and a shaft extending from the second end of the head to a third end along the central longitudinal axis, the shaft including an elongated fixation element hole elongated in a direction parallel to the central longitudinal axis.

BRIEF DESCRIPTION OF THE DRAWINGS

Several embodiments will be described in the following by way of example and with reference to the accompanying drawings in which.

DETAILED DESCRIPTION

Figure 1:
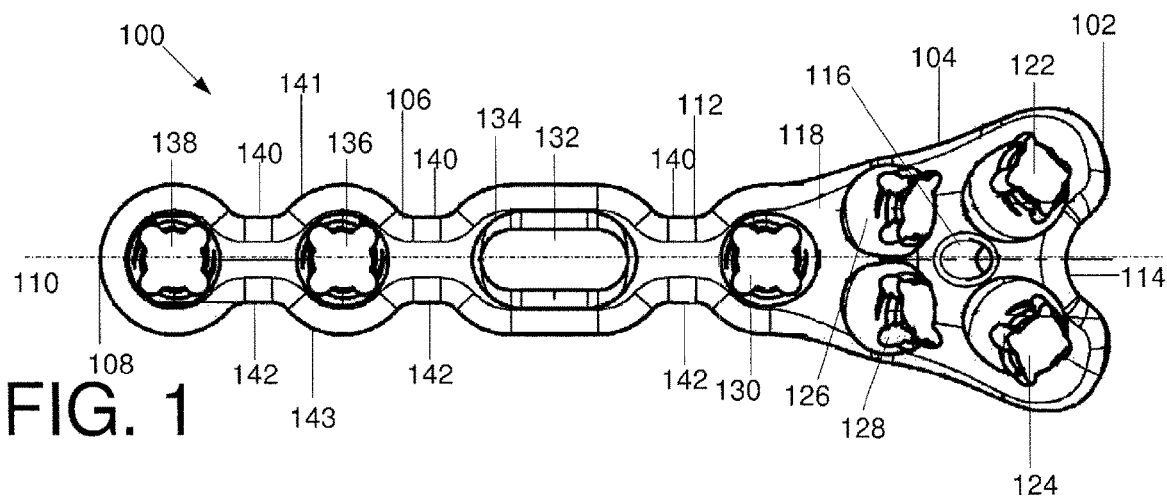
FIG. 1 shows a first perspective view of a bone plate according to an exemplary embodiment.

The exemplary embodiments may be further understood with reference to the following description and the appended drawings, wherein like elements are referred to with the same reference numerals. The exemplary embodiments relate to apparatus and methods for the treatment of fractures and, in particular, to devices for fixing fracture of the fifth metacarpal. More specifically, the exemplary bone fixation plates may be used for the fixation of unstable subcapital comminuted head and neck fractures of the metacarpals. Exemplary embodiments describe a bone fixation plate having a head and an elongated shaft, which plate is positionable against an outer surface of a fractured or otherwise damaged bone. The exemplary head of the bone plate is formed in a "y" shape having first and second sides separated by a substantially rounded notch aligned with a central longitudinal axis of the plate. The notch is sized and shaped so that when the plate is positioned over a target portion of the fifth metacarpal, a collateral ligament is received in notch, limiting interference from the plate with surrounding ligaments and tissues. The head includes five variable angle fixation element holes in a grid formation and having hole axes diverging away from one another, as will be described in greater detail later on. A bone contacting surface of the head is formed with a curvature selected to conform to a curvature of the metacarpal to ensure flush seating of the plate thereover. The head further includes a guide wire hole sized and shaped to receive a guide wire such as a Kirschner wire. The shaft is formed with a webbed shape and has a plurality of variable angle fixation element holes and an elongated compression hole. As will be described in greater detail later on, the exemplary shape, size and contour of the exemplary bone plate permits the bone plate to be positioned further dorsally on the fifth metacarpal than plates in currently available systems. It is noted that although the exemplary system and method are directed to fixation of fractures of a fifth metacarpal, the exemplary bone fixation system may be used in any other metacarpal without deviating from the scope of the invention. It should be noted that the terms "proximal" and "distal" as used herein, refer to a direction toward (proximal) and away from (distal) a core of the body. For example, a direction from the hand to the elbow is proximal while a direction from the elbow to the hand is distal. Furthermore, when using these terms in reference to a plate to be attached to a bone, proximal will refer to a direction along the plate when it is attached to a target bone in a desired orientation.

Figure 2:
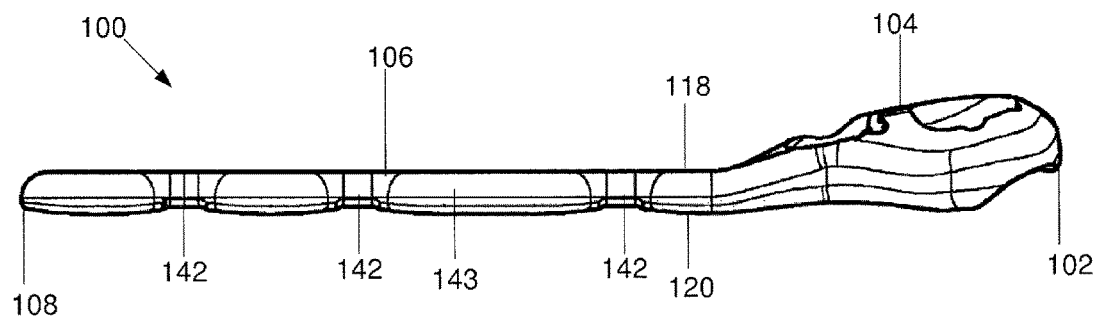
FIG. 2 shows a first lateral view of the bone plate of FIG. 1.
Figure 3:
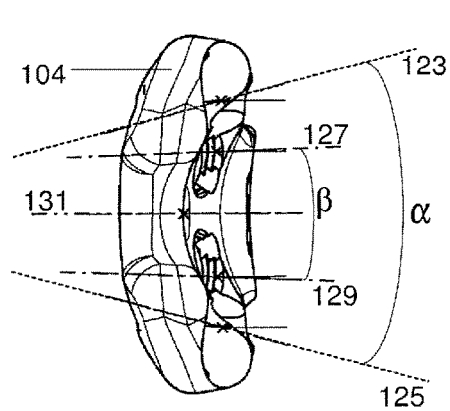
FIG. 3 shows a second lateral view of the bone plate of FIG. 1.

As shown in FIGS. 1-3, an exemplary bone plate 100 extends from a first end 102 including a head 104 to a second end 106 including a shaft 108 along a central longitudinal axis 110. The head 104 has a substantially triangular shape with a first width at the first end 102 and a second, smaller width at a junction portion 112. A notch 114 at the first end 102 has a substantially rounded shape and is substantially aligned with the longitudinal axis 110. In an exemplary embodiment, a shape of the notch 114 corresponds to an arc of a circle. In one embodiment, the notch 114 has a radius of curvature of 1.5 mm. However, alternative embodiments may be formed with a radius of curvature of up to 3 mm without deviating from the scope of the invention. As would be understood by those skilled in the art, a radius of curvature of the notch 114 may be selected to correspond to dimensions of a ligament to be received in the notch when the plate 100 is implanted. For example, the notch 114 may be sized such that, when implanted on a fifth metacarpal, a collateral ligament attaches to the bone at a point within the notch 114, so that the ligament passes over the plate 100 minimizing the discomfort associated with interference from the bone plate with ligaments post-implantation while permitting placement of the bone plate 100 further dorsally on the bone. In another embodiment, the notch 114 may have a non-circular shape (e.g., oblong, etc.) without deviating from the scope of the invention.

The head 104 also includes a K-wire hole 116 extending therethrough to guide placement of the bone plate 100 over a target portion of the bone. As those skilled in the art will understand, K-wires are not conventionally passed through bone plates for the fixation of metacarpal fractures. In contrast, conventional bone plates for the fixation of metacarpal fractures are typically manually positioned over the bone and held in place by hand or with forceps. In an exemplary embodiment, the K-wire hole 116 is aligned with the central longitudinal axis 110 and extends from the top surface 118 to a bone contacting surface 120 at an angle that is not orthogonal to the top surface 118. In a preferred embodiment, the K-wire hole 116 is angled so that an end of a wire which has passed through the hole 116 toward the bone will extend toward the end of the plate 100 including the notch 114. The K-wire hole 116 according to this embodiment has a diameter of, for example, 1.0 mm to accommodate K-wires having a diameter of 1.0 mm or smaller.

The bone contacting surface 120 of the head 104 is formed with a curvature selected to conform to the curvature of the metacarpal to ensure flush seating of the bone plate thereover. In one embodiment, the bone contacting surface 120 of the head 104 has a radius of curvature of 5 mm. In another embodiment, the bone-contacting surface 120 includes a plurality of curvatures corresponding to the surface of the bone.

The head 104 also comprises a plurality of fixation element holes 122, 124, 126, 128, 130. The fixation element holes 122, 124, 126, 128 extend through the plate 100 along hole axes angled to diverge from one another on a bone facing side of the plate 100. The holes 122, 124 are symmetrically positioned with respect to the longitudinal axis 110 and extend through the bone plate 100 at opposing angles. For example, in one embodiment, the hole axes 123, 125 of the fixation element holes 122, 124, respectively, enclose an angle α of 31 degrees. It is noted, however, that this value is exemplary only and a plurality of other values for α may be employed without deviating from the scope of the invention. For example, the angle α may be 0-45 degrees. The fixation element holes 126, 128 are also symmetrical with respect to the longitudinal axis 110 and extend through the bone plate 100 at opposing angles. For example, in one embodiment the hole axes 127, 129 of the fixation element holes 126, 128, respectively, enclose an angle β of 4 degrees. It is noted, however, that this value is exemplary only and a plurality of other values for β may be employed without deviating from the scope of the invention. For example, the angle β may be 0-10 degrees. The four diverging screw trajectories defined by bone plate hole axes 123, 125, 127, 129 are designed to capture common fracture patterns of the metacarpals while avoiding the articular surface of the bone. The fixation element holes 122, 124, 126, 128 are formed as variable angle holes to permit the bone screws to be locked at any angulation within a predefined range of angulation (e.g., ±15°) relative to their hole axes 123, 125, 127, 129 as would be understood by those skilled in the art. This configuration permits the surgeon to alter the angle of insertion as needed to capture hard to reach fracture fragments. The fixation element hole 130 is centered about the longitudinal axis 110 and is also formed as a variable angle hole with substantially the same structure and operation as the fixation element holes 122, 124, 126, 128 described above. A bone plate hole axis 131 of the bone plate hole 130 extends orthogonally to the top surface 118. In this embodiment, the fixation element holes 122, 124, 126, 128, 130 are sized to lockingly receive the heads of 1.5 mm variable angle locking screws, although other dimensions are envisioned within the scope of the invention.

The shaft 106 includes an elongated compression hole 132 centered on the shaft 106 and elongated in a direction parallel to the longitudinal axis 110. The compression hole 132 allows for plate adjustment after a bone screw (not shown) has been provisionally inserted therethrough into the bone (i.e., prior to tightening of the bone screw within the compression hole 132). The compression hole 132 includes an increased diameter lip 134 formed to seat an enlarged diameter head of a bone screw (not shown) therein. The shaft 106 also includes variable angle fixation element holes 136, 138 having bone plate hole axes extending orthogonal to the top surface 118, wherein bone screws inserted through the fixation element holes 136, 138 may be angled within a predetermined range relative to the bone plate hole axes, as described in greater detail above. The fixation element holes 136, 138 are also centered about the longitudinal axis 110. The fixation element holes 136, 138 in this embodiment are also sized to lockingly receive the heads of 1.5 mm variable angle locking screws, although other dimensions are envisioned within the scope of the invention.

Figure 4:
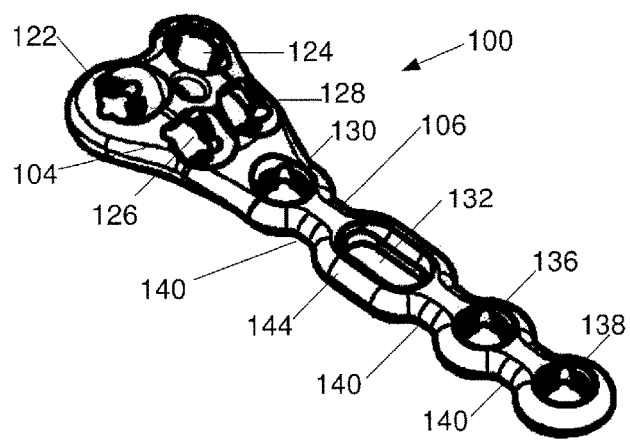
FIG. 4 shows a second perspective view of the bone plate of FIG. 1.

The shaft 106 also includes a plurality of first webbed portions 140 extending along a first side wall 141 between each of the holes 130, 132, 136, 138 and a plurality of second webbed portions 142 extending along a second side wall 143 between each of the holes 130, 132, 136, 138. The first and second webbed portions 140, 142 are formed as notches extending into the bone plate 100 to reduce a profile thereof while maintaining the structural integrity of the bone plate 100. The first and second webbed portions 140, 142 are sized such that a minimum clearance remains at the boundary of each of the plate holes 130, 132, 136, 138. As shown in FIG. 4, the outer periphery 144 of the bone plate 100 may include a rounded taper to further reduce the profile.

In accordance with an exemplary method, a K-wire (not shown) is inserted into a target portion of the bone. The free end of the K-wire is slidably received in the K-wire hole 116 to guide provisional positioning of the bone plate 100 over the bone. In an exemplary embodiment, the bone plate 100 is positioned over a lateral surface of the fifth metacarpal or on a dorsolateral surface of the second, third or fourth metacarpal. The head 104 is positioned over the neck of the metacarpal while the shaft extends distally therefrom (i.e., in a direction extending toward a distal end of the finger). A bone fixation element such as a bone screw (not shown) is then inserted into the compression hole 132. The bone plate 100 may then be repositioned if needed by sliding the bone plate 100 over the bone within a range of motion defined by the length of the compression hole 132. Once the bone plate 100 has been moved to a desired final position over the bone, bone screws (not shown) are inserted into one or both of the fixation element holes 122, 124, followed by insertion of bone screw (not shown) into any of the fixation element holes 126, 128, 130, 136, 138 in accordance with the requirements of the procedure (e.g., according to the fracture pattern).

It will be appreciated by those skilled in the art that various modifications and alterations of the disclosed embodiments may be made without departing from the broad scope of the invention. Some of these have been discussed above and others will be apparent to those skilled in the art.

What is claimed is:

1. A bone plate sized and shaped for fixation to a metacarpal, comprising:

a head extending from a first end to a second end and having first and second fixation element holes extending therethrough along first and second fixation element hole axes, wherein the first hole axis diverges from the second hole axis on a bone facing side of the plate, the head having a first notch on the first end centered on the central longitudinal axis, the first notch formed as a indentation on an outer wall of the bone plate sized and shaped to accommodate a collateral ligament when the plate is fixed to a metacarpal in a desired position; and a shaft extending from the second end of the head to a third end along the central longitudinal axis, the shaft including an elongated fixation element hole elongated in a direction parallel to the central longitudinal axis.

2. The bone fixation plate of claim 1, wherein a shape of the bone facing surface of the head conforms to a contour of a metacarpal to which it is to be fixed.

3. The bone fixation plate of claim 1, wherein the head and shaft are sized and shaped for fixation laterally over a fifth metacarpal.

4. The bone fixation plate of claim 1, wherein the head further comprises third and fourth fixation element holes extending therethrough along third and fourth hole axes, respectively, wherein the first, second, third and fourth hole axes diverge from one another on the bone facing side of the head.

5. The bone fixation plate of claim 4, wherein the third and fourth fixation element holes are symmetric with respect to the central longitudinal axis, the third hole axis being complementary to the fourth hole axis.

6. The bone fixation plate of claim 5, wherein the head further comprises a fifth fixation element hole having defining a fifth hole axis orthogonal to a plane in which the shaft is located.

7. The bone fixation plate of claim 6, wherein the shaft includes sixth and seventh fixation element holes extending therethrough along sixth and seventh hole axes, respectively.

8. The bone fixation plate of claim 7, wherein the shaft includes plurality of second notches formed in first and second lateral walls thereof, the second notches defining reduced width regions of the shaft.

9. The bone fixation plate of claim 8, wherein the second notches are located along the length of the shaft between adjacent ones of the fourth fixation element hole, the elongated hole, the sixth fixation element hole and the seventh fixation element hole.

10. The bone fixation plate of claim 1, wherein the head is angled away from a plane of the shaft.

11. The bone fixation plate of claim 1, further comprising a tapered region extending around a periphery of the bone plate to reduce a profile thereof.

12. The bone fixation plate of claim 1, wherein the first and second hole axes are symmetric with respect to the central longitudinal axis, the first hole axis being complementary to the second hole axis.

13. The bone fixation plate of claim 1, further comprising a guide-wire hole extending through the head.

* * * * *